United States Patent
Shimizu

(10) Patent No.: US 10,258,767 B2
(45) Date of Patent: Apr. 16, 2019

(54) CATHETER

(71) Applicant: ASAHI INTECC CO., LTD., Seto-shi, Aichi (JP)

(72) Inventor: Hirotomo Shimizu, Nagoya (JP)

(73) Assignee: ASAHI INTECC CO., LTD., Seto-shi (JP)

( * ) Notice: Subject to any disclaimer, the term of this patent is extended or adjusted under 35 U.S.C. 154(b) by 0 days.

(21) Appl. No.: 15/462,082

(22) Filed: Mar. 17, 2017

(65) Prior Publication Data

US 2018/0056037 A1 Mar. 1, 2018

Related U.S. Application Data

(63) Continuation of application No. PCT/JP2016/075683, filed on Sep. 1, 2016.

(51) Int. Cl.
*A61M 25/00* (2006.01)
*A61M 25/01* (2006.01)

(52) U.S. Cl.
CPC ...... *A61M 25/0052* (2013.01); *A61M 25/008* (2013.01); *A61M 25/0069* (2013.01); *A61M 25/0108* (2013.01); *A61M 25/001* (2013.01); *A61M 25/005* (2013.01)

(58) Field of Classification Search
CPC .......... A61M 25/0052; A61M 25/0108; A61M 25/008; A61M 25/005; A61M 25/0053
See application file for complete search history.

(56) References Cited

U.S. PATENT DOCUMENTS

| 5,221,270 | A | | 6/1993 | Parker |
| 5,700,253 | A | * | 12/1997 | Parker ............... A61M 25/0012 604/524 |
| 5,702,373 | A | * | 12/1997 | Samson ............... A61M 25/005 604/526 |
| 5,769,830 | A | | 6/1998 | Parker |
| 8,858,530 | B2 | * | 10/2014 | Nishigishi ......... A61M 25/0053 138/123 |

FOREIGN PATENT DOCUMENTS

| EP | 0 520 692 B1 | 8/1996 |
| EP | 0 537 895 B1 | 11/1996 |
| EP | 2 213 325 B1 | 11/2016 |
| JP | H07-008563 A | 1/1995 |
| JP | 2008-229160 A | 10/2008 |
| JP | 2010-137095 A | 6/2010 |

* cited by examiner

*Primary Examiner* — Lauren P Farrar

(57) ABSTRACT

A catheter having a catheter shaft and a tip. The catheter shaft includes an inner layer, a first reinforcing layer disposed around an outer periphery of the inner layer, an intermediate layer, a second reinforcing layer disposed around an outer periphery of the intermediate layer, and an outer layer that covers the second reinforcing layer. The tip includes a proximal end portion that extends in an axial direction of the catheter and is joined to at least the intermediate layer and the outer layer, between the first reinforcing layer and the second reinforcing layer. The proximal end portion increases the joining strength between the intermediate layer and the tip and the joining strength between the outer layer and the tip. As a result, it is possible to prevent the tip from easily detaching from the catheter shaft.

13 Claims, 15 Drawing Sheets

CATHETER

CROSS REFERENCE TO RELATED APPLICATION

This application is a continuation of PCT/JP2016/075683 filed on Sep. 1, 2016, the contents of which are incorporated by reference herein in their entirety.

BACKGROUND

The disclosed embodiments relate to a medical device. Specifically, the disclosed embodiments relate to a catheter in which a tip is joined to a distal end of a catheter shaft.

When a stenosis site or blockage is formed in a blood vessel, a bile duct, a pancreatic duct, or the like, the flow of blood, gall (bile), pancreatic juice, or the like, respectively, is disrupted. As a method of treating such a stenosis site or blockage, a treatment using a catheter is widely performed.

Generally in a catheter, a flexible tip is joined to a distal end of a catheter shaft including a reinforcing layer (see U.S. Pat. No. 5,769,830, for example). In this manner, the rigid catheter shaft maintains the operability of the catheter, while the flexible tip reduces potential damage to duct walls of a blood vessel, a bile duct, a pancreatic duct, or the like when the catheter is inserted therein.

However, in such a catheter, the tip is only joined to the distal end of the catheter shaft. The joining strength between the catheter shaft and the tip is small, and the tip can detach from the catheter shaft when a technician operates the catheter while the tip is caught by a stenosis site or blockage.

Moreover, when the catheter is inserted into a highly bent blood vessel, bile duct, pancreatic duct, or the like, stress is concentrated at a boundary portion between the tip and the catheter shaft, which can cause the tip to break at the boundary portion.

SUMMARY

In view of such problems, the disclosed embodiments aim to provide a catheter in which a tip is hardly removed from a catheter shaft and hardly breaks at a boundary portion between the tip and the catheter shaft.

The above-described problems are addressed by a catheter having the following structure.

A catheter of the disclosed embodiments includes a catheter shaft and a tip joined to a distal end of the catheter shaft. The catheter shaft has an inner layer, a first reinforcing layer wound on (disposed around) an outer periphery of the inner layer, an intermediate layer covering the first reinforcing layer, a second reinforcing layer wound on (disposed around) an outer periphery of the intermediate layer, and an outer layer covering the second reinforcing layer. The tip includes a proximal end portion that extends proximally in an axial direction of the catheter and is joined to at least one of the intermediate layer and the outer layer, between the first reinforcing layer and the second reinforcing layer.

The above-discussed configuration increases the joining strength between the catheter shaft and the tip; specifically, the joining strength between the intermediate layer and the tip and/or between the outer layer and the tip is increased. As a result, it is possible to prevent the tip from easily detaching from the catheter shaft. Moreover, the proximal end portion extends proximally in the axial direction, which can reduce a risk that the tip will break at the boundary portion even when stress is concentrated at the boundary portion between the tip and the catheter shaft.

The intermediate layer may include an uneven outer peripheral surface, the outer layer may include an uneven inner peripheral surface, and the proximal end portion of the tip may be joined to at least one of the uneven outer peripheral surface of the intermediate layer and the uneven inner peripheral surface of the outer layer. The anchoring effect with the uneven surface increases the joining strength between the catheter shaft and the tip, and it is possible to further prevent the tip from easily detaching from the catheter shaft.

The thickness of the proximal end portion of the tip may increase in the distal direction. Thus, it is possible to further reduce a risk that the tip will break at the boundary portion even when stress is concentrated at the boundary portion between the tip and the catheter shaft.

DETAILED DESCRIPTION OF EMBODIMENTS

Figure 1:
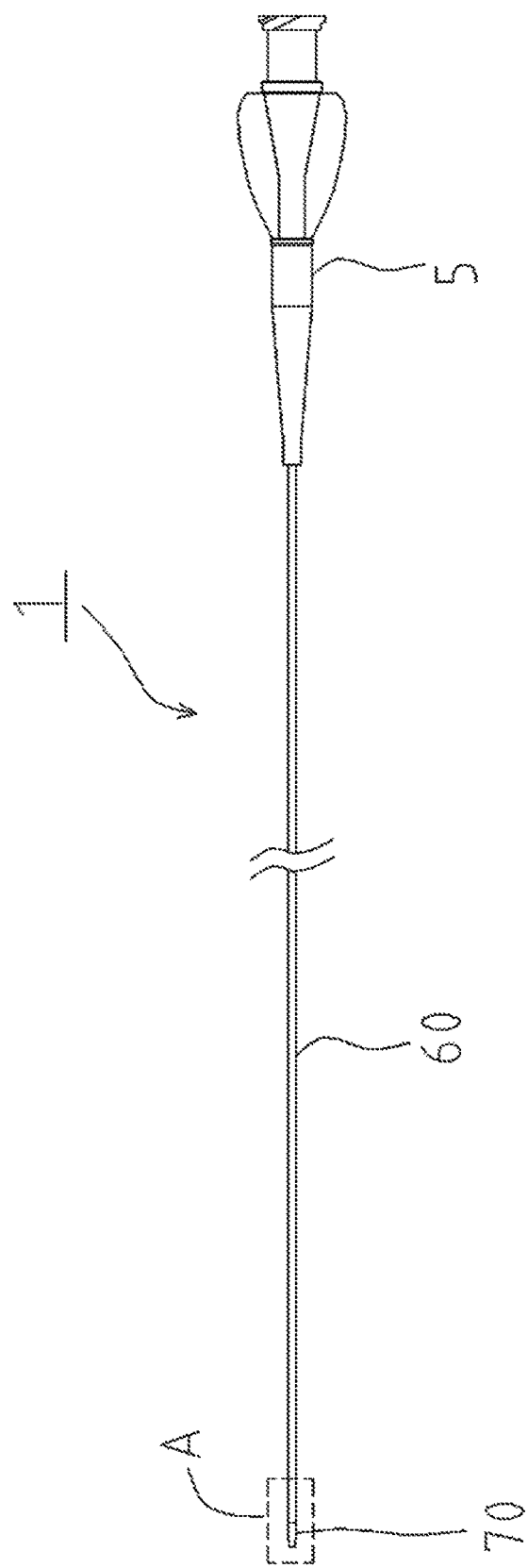
FIG. 1 is a diagram illustrating an entire view of a catheter according to the disclosed embodiments.
Figure 2:
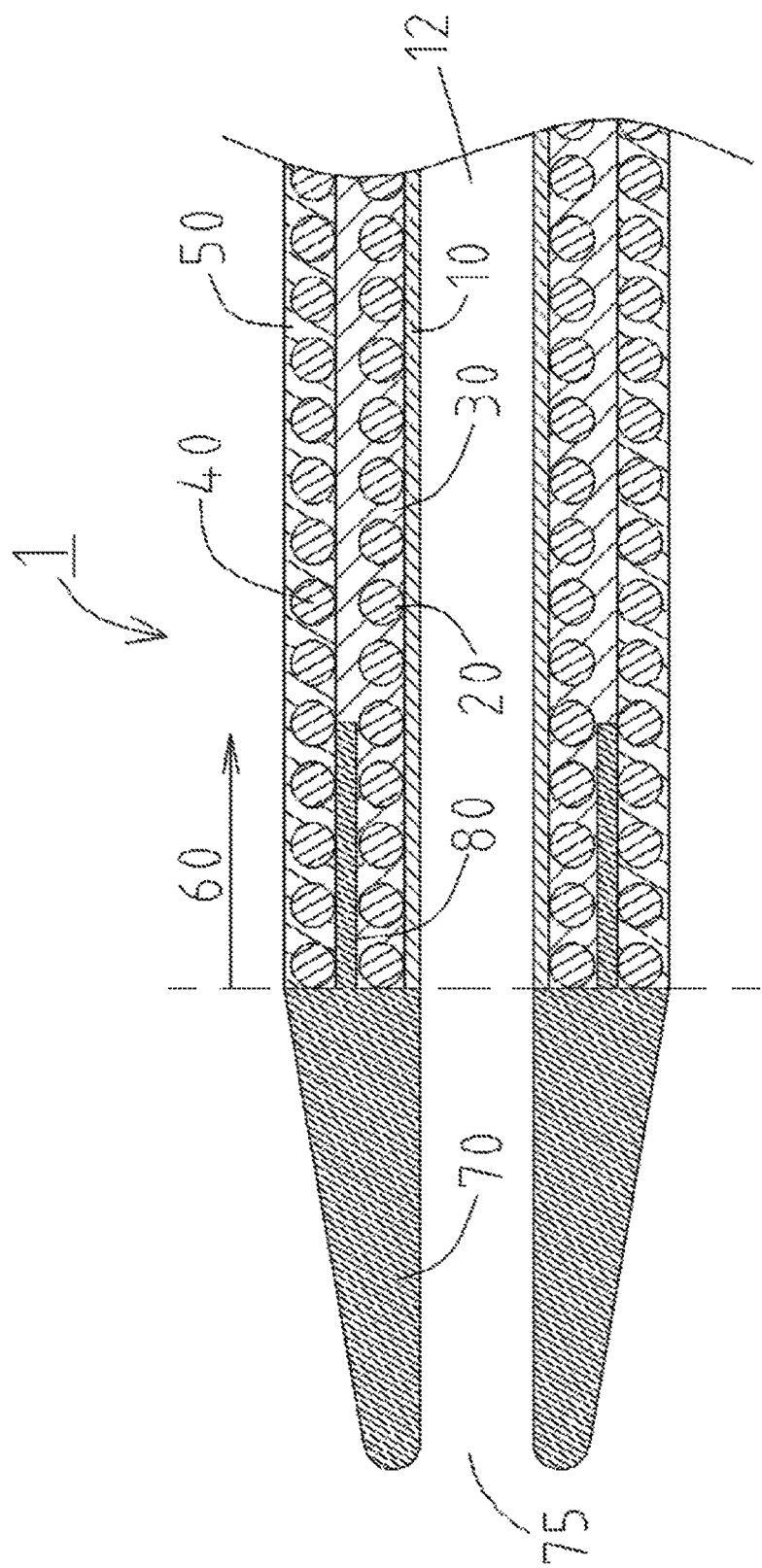
FIG. 2 is an enlarged cross-sectional view of part A shown in FIG. 1.

A catheter 1 according to the disclosed embodiments will be described with reference to FIG. 1 and FIG. 2. FIG. 1 is a diagram illustrating an entire view of the catheter 1. FIG. 2 is an enlarged cross-sectional view of part A shown in FIG. 1. Throughout the figures, the left side of the drawings corresponds to a distal end (front end) to be inserted into a body, while the right side corresponds to a proximal end (rear end) to be operated by a technician such as a physician.

The catheter 1 is a catheter used for treating a stenosis site or blockage. As illustrated in FIG. 1, the catheter 1 includes a catheter shaft 60, a tip 70 joined to a distal end of the catheter shaft 60, and a connector 5 joined to a proximal end of the catheter shaft 60.

The catheter shaft 60 includes, in order from an inner side in a radial direction, an inner layer 10, a first coil body 20 that is a first reinforcing layer wound on an outer periphery of the inner layer 10, an intermediate layer 30 covering the first coil body 20, a second coil body 40 that is a second reinforcing layer wound on an outer periphery of the intermediate layer 30, and an outer layer 50 covering the second coil body 40, as illustrated in FIG. 2.

The inner layer 10 is formed of resin, and forms a lumen 12 into which a guide wire or another catheter may be inserted. The resin material forming the inner layer 10 is not particularly limited. Polytetrafluoroethylene (PTFE) may be used.

The first coil body 20 is formed on the outer periphery of the inner layer 10. Such a first coil body 20 is wound in a clockwise direction toward the distal end. As the material forming the first coil body 20, stainless steel (SUS304) is used for purposes of this discussion. However, the coil body 20 is not limited to this material. For example, a metal material such as tungsten or an Ni—Ti alloy may be used, or a resin material such as reinforced plastic (e.g., polyether ether ketone, known as PEEK).

The intermediate layer 30 is formed of resin and is formed on the outer periphery of the first coil body 20, and covers the inner layer 10 and the first coil body 20. The resin material forming the intermediate layer 30 is not particularly limited, and polyamide, polyamide elastomer, polyester, polyurethane, and the like can be used.

The second coil body 40 is formed on the outer periphery of the intermediate layer 30. This second coil body 40 is wound in a counterclockwise direction toward the distal end, which is a direction opposite to the winding direction of the first coil body 20. As the material forming the second coil body 40, a metal material such as stainless steel (SUS304), tungsten, or an Ni—Ti alloy may be used, or a resin material such as reinforced plastic (PEEK) may be used, similarly to the first coil body 20.

The outer layer 50 is formed of resin and is formed on the outer periphery of the second coil body 40, and covers the intermediate layer 30 and the second coil body 40. The resin material forming the outer layer 50 is not particularly limited, and polyamide, polyamide elastomer, polyester, polyurethane, and the like can be used, similarly to the intermediate layer 30.

The tip 70 is formed of resin and is joined to the distal end of the catheter shaft 60. The tip 70 is a cylindrical member having a distal end opening 75 communicating with the lumen 12. The resin forming the tip 70 is not particularly limited, and polyurethane, polyurethane elastomer, and the like may be used. Moreover, the tip 70 may contain radiopaque powder. For example, when the tip 70 contains radiopaque powder (e.g., tungsten powder) in a range of about 65 w % to about 90 w %, the technician such as a physician can accurately determine a position of the catheter 1 in coronary angiography.

This tip 70 includes a proximal end portion 80 that extends proximally in an axial direction of the catheter 1 and is joined to at least the intermediate layer 30 and the outer layer 50, between the first coil body 20 and the second coil body 40 (see FIG. 2). In this manner, the proximal end portion 80 is joined to the intermediate layer 30 and the outer layer 50, which increases the joining strength between the intermediate layer 30 and the tip 70 and the joining strength between the outer layer 50 and the tip 70. In other words, the joining strength between the catheter shaft 60 and the tip 70 is increased. As a result, it is possible to prevent the tip 70 from easily detaching from the catheter shaft 60.

Moreover, even when stress is concentrated at the boundary portion between the tip 70 and the catheter shaft 60, the proximal end portion 80 can reduce a risk that the tip 70 will break at the boundary portion. Furthermore, when the technician rotates the catheter 1 in a clockwise direction, the first coil body 20 wound in a clockwise direction is loosened and expands in a radial direction, while the second coil body 40 wound in a counterclockwise direction is tightened and shrinks in a radial direction. Thus, even when the catheter 1 is operated while the tip 70 is caught by a stenosis site or blockage, the proximal end portion 80 of the tip 70 is pressed by the first coil body 20 and the second coil body 40 by operating the catheter 1 while rotating it in a clockwise direction, which prevents the tip 70 from detaching from the catheter shaft 60.

Next, a catheter 2 of the disclosed embodiments will be described with reference to FIG. 3. Explaining only differences from the catheter 1 illustrated in FIG. 2, the catheter 2 includes a first braid 22 as a first reinforcing layer instead of the first coil body 20.

In this first braid 22, pieces of first wire and pieces of second wires are mutually woven in a net form (mesh form). That is, 16 total pieces of wire including eight pieces of first wire and eight pieces of second wire (8 pieces×8 pieces) are woven alternately.

The material of the first wire and the material of the second wire forming the first braid 22 may be the same or different. The first wire may be formed of tungsten and the second wire may be formed of stainless steel (SUS304). However, the materials are not particularly limited thereto, and a resin material other than metal (e.g., reinforced plastic) may be used.

Figure 3:
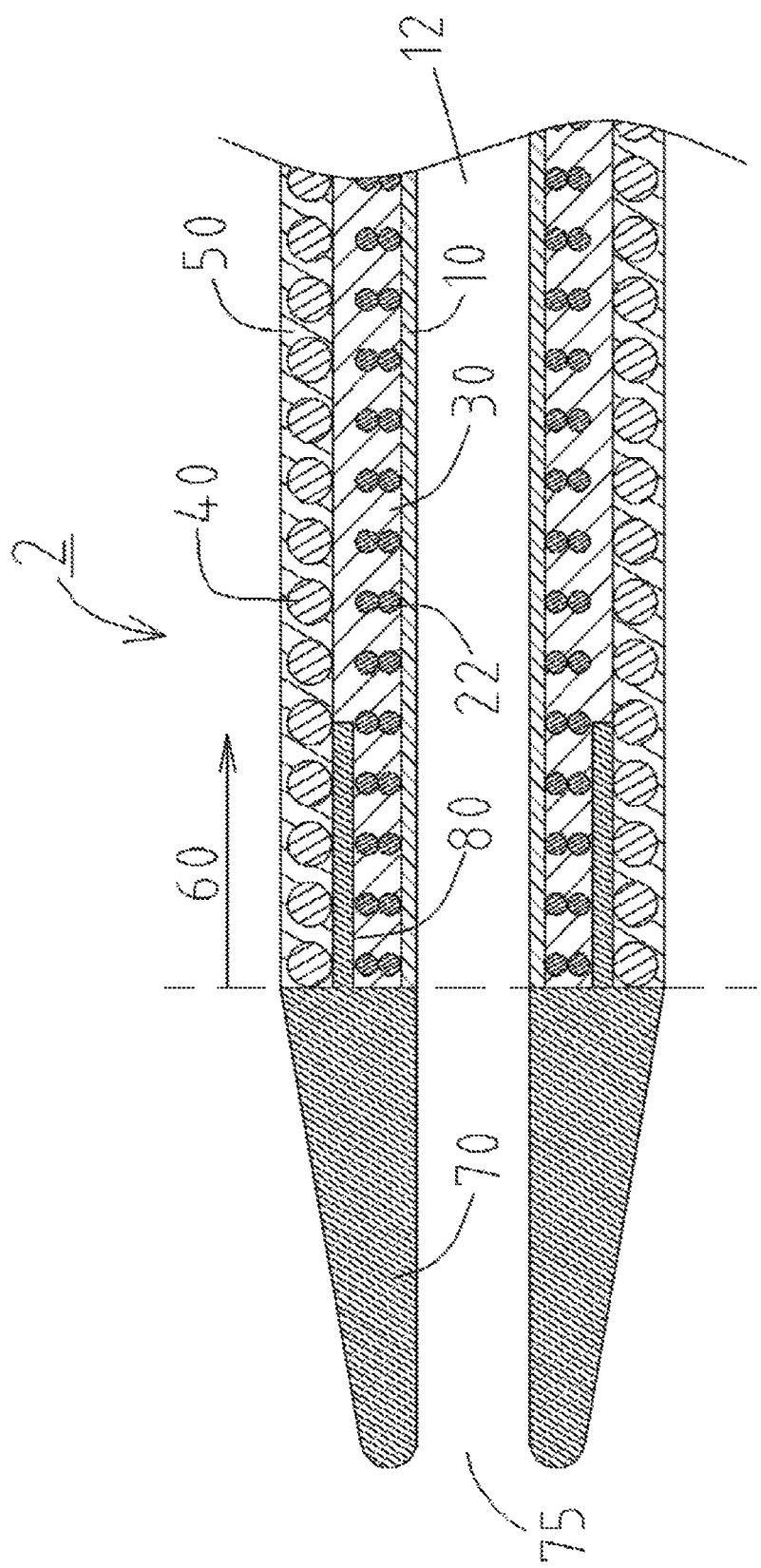
FIG. 3 is a cross-sectional view illustrating a part of a catheter according to the disclosed embodiments.

The catheter 2 includes the proximal end portion 80 that extends proximally in an axial direction of the catheter 2 and is joined to at least one of the intermediate layer 30 and the outer layer 50, between the first braid 22 and the second coil body 40 (see FIG. 3). In this manner, the proximal end portion 80 is joined to the intermediate layer 30 and the outer layer 50, which increases the joining strength between the intermediate layer 30 and the tip 70 and the joining strength between the outer layer 50 and the tip 70, similarly to the catheter 1. In other words, the joining strength between the catheter shaft 60 and the tip 70 is increased. As a result, it is possible to prevent the tip 70 from easily detaching from the catheter shaft 60.

Next, a catheter 3 of the disclosed embodiments will be described with reference to FIG. 4. Explaining only differences from the catheter 2 illustrated in FIG. 3, the catheter 3 includes a second braid 42 as the second reinforcing layer instead of the second coil body 40.

In this second braid 42, pieces of first wire and pieces of second wire are mutually woven in a net form (mesh form), similarly to the first braid 22. A total of 16 pieces (8 pieces×8 pieces) of wire including eight pieces of first wire and eight pieces of second wire are woven alternately.

The material of the first wire and the material of the second wire forming the second braid 42 may be the same or different. The first wire may be formed of tungsten and the second wire may be formed of stainless steel (SUS304). However, the materials are not particularly limited thereto, and a resin material other than metal (e.g., reinforced plastic) may be used.

Figure 4:
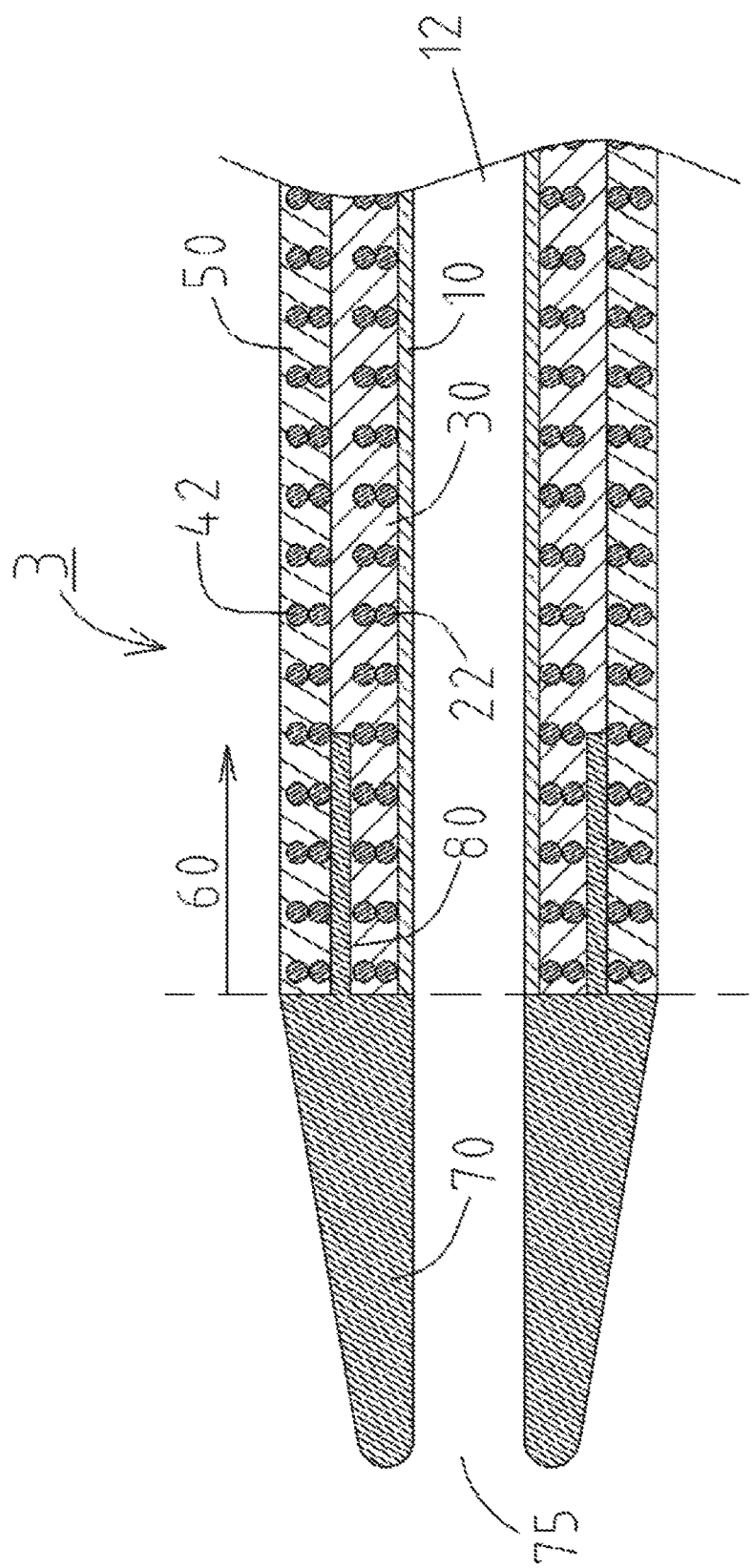
FIG. 4 is a cross-sectional view illustrating a part of a catheter according to the disclosed embodiments.

The catheter 3 includes the proximal end portion 80 that extends in an axial direction of the catheter 3 and is joined to at least one of the intermediate layer 30 and the outer layer 50, between the first braid 22 and the second braid 42 (see FIG. 4). In this manner, the proximal end portion 80 is joined to the intermediate layer 30 and the outer layer 50, which increases the joining strength between the intermediate layer 30 and the tip 70 and the joining strength between the outer layer 50 and the tip 70, similarly to the catheters 1, 2. In other words, the joining strength between the catheter shaft 60 and the tip 70 is increased. As a result, it is possible to prevent the tip 70 from easily detaching from the catheter shaft 60.

Figure 5:
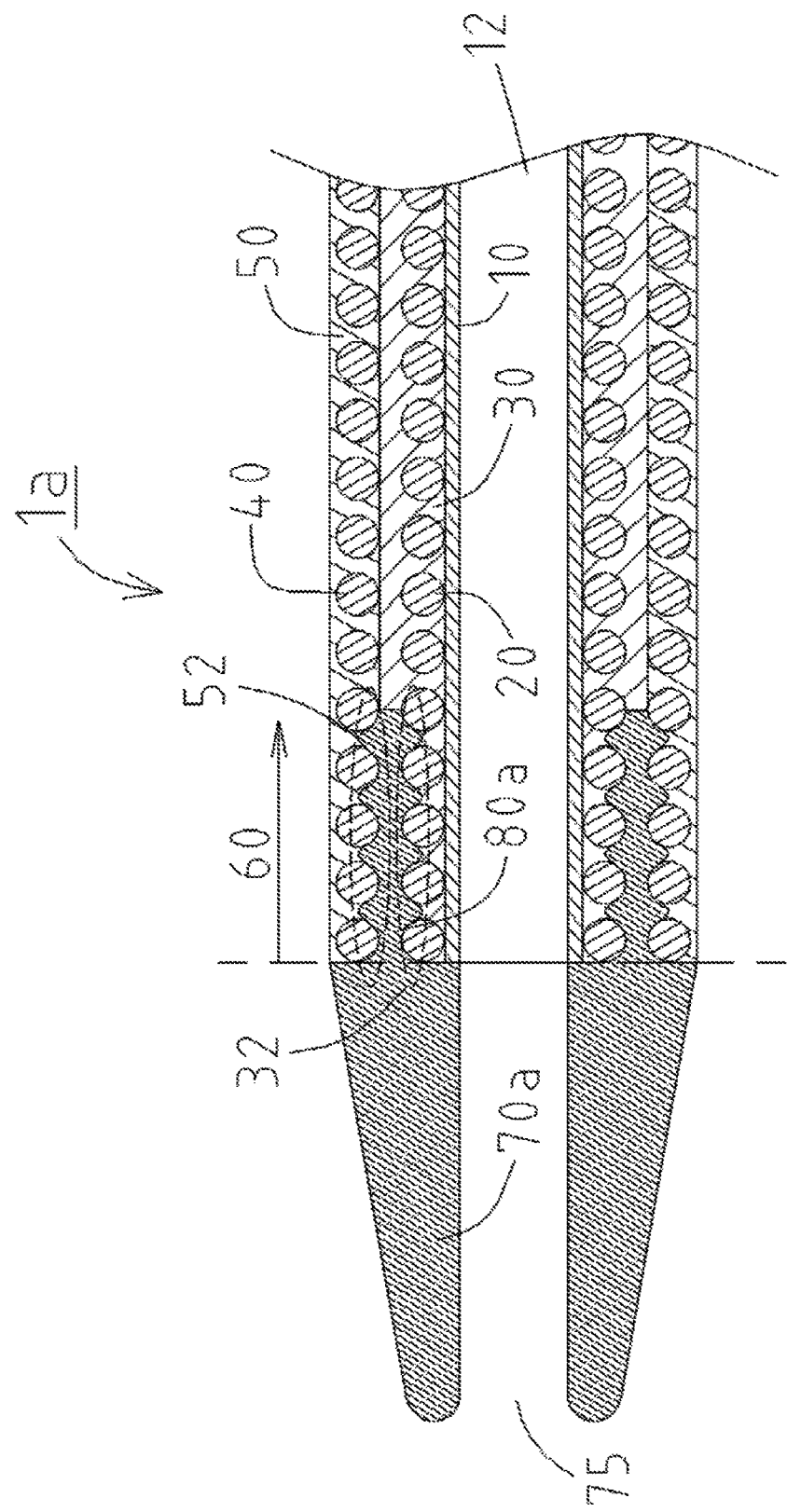
FIG. 5 is a cross-sectional view illustrating a part of a catheter according to the disclosed embodiments.

Next, a catheter 1a of the disclosed embodiments will be described with reference to FIG. 5. Explaining only differences from the catheter 1 illustrated in FIG. 2, in the catheter 1a, the intermediate layer 30 includes an uneven outer peripheral surface 32, and the outer layer 50 includes an uneven inner peripheral surface 52 (see FIG. 5). A tip 70a includes a proximal end portion 80a joined to the outer peripheral surface 32 of the intermediate layer 30 and the inner peripheral surface 52 of the outer layer 50, between the first coil body 20 and the second coil body 40. The anchoring effect between the proximal end portion 80a and the outer peripheral surface 32 of the intermediate layer 30 and the anchoring effect between the proximal end portion 80a and the inner peripheral surface 52 of the outer layer 50 increase the joining strength between the intermediate layer 30 and the tip 70a and the joining strength between the outer layer 50 and the tip 70a, respectively. In other words, the joining strength between the catheter shaft 60 and the tip 70a is increased. As a result, it is possible to further prevent the tip 70a from easily detaching from the catheter shaft 60.

Figure 6:
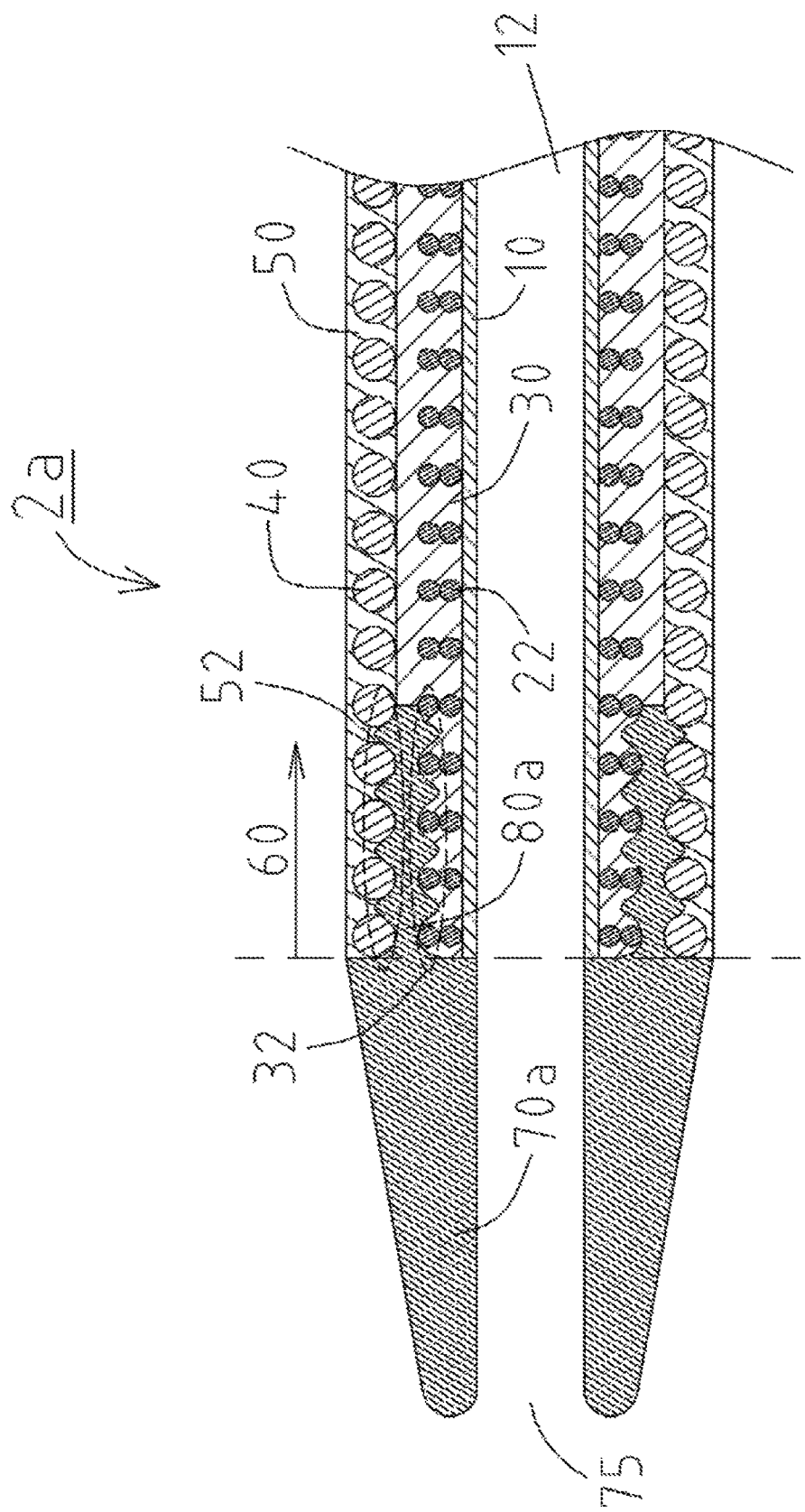
FIG. 6 is a cross-sectional view illustrating a part of a catheter according to the disclosed embodiments.

Next, a catheter 2a of the disclosed embodiments will be described with reference to FIG. 6. Explaining only differences from the catheter 2 illustrated in FIG. 3, in the catheter 2a, the intermediate layer 30 includes the uneven outer peripheral surface 32, and the outer layer 50 includes the uneven inner peripheral surface 52 (see FIG. 6). The tip 70a includes the proximal end portion 80a joined to the outer peripheral surface 32 of the intermediate layer 30 and the inner peripheral surface 52 of the outer layer 50, between the first braid 22 and the second coil body 40. The anchoring effect between the proximal end portion 80a and the outer peripheral surface 32 of the intermediate layer 30 and the anchoring effect between the proximal end portion 80a and the inner peripheral surface 52 of the outer layer 50 increase the joining strength between the intermediate layer 30 and the tip 70a and the joining strength between the outer layer 50 and the tip 70a, respectively. In other words, the joining strength between the catheter shaft 60 and the tip 70a is increased. As a result, it is possible to further prevent the tip 70a from easily detaching from the catheter shaft 60.

Figure 7:
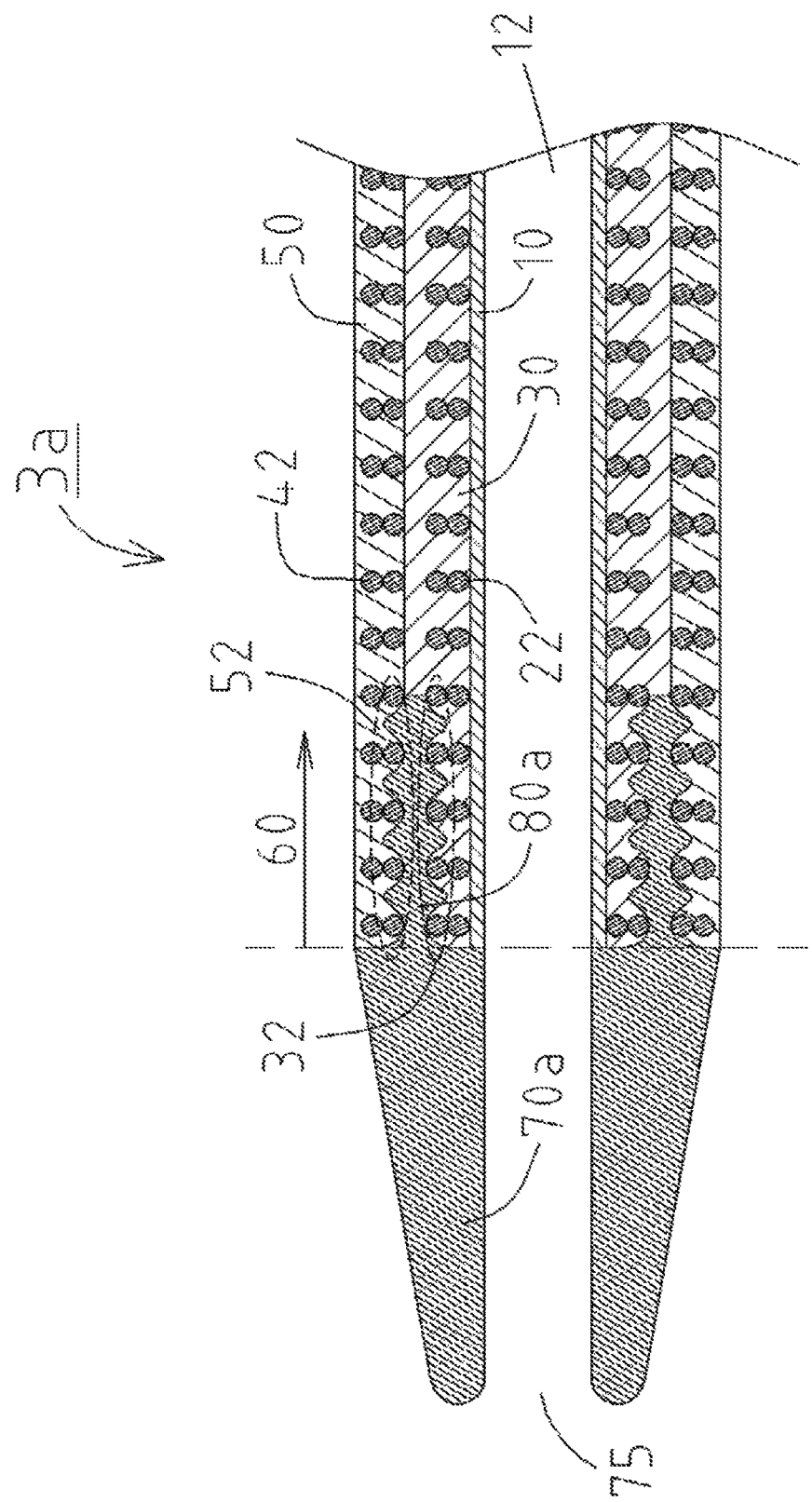
FIG. 7 is a cross-sectional view illustrating a part of a catheter according to disclosed embodiments, and is a first modification of FIG. 4.

Next, a catheter 3a of the disclosed embodiments will be described with reference to FIG. 7. Explaining only differences from the catheter 3 illustrated in FIG. 4, in the catheter 3a, the intermediate layer 30 includes the uneven outer peripheral surface 32, and the outer layer 50 includes the uneven inner peripheral surface 52 (see FIG. 7). The tip 70a includes the proximal end portion 80a joined to the outer peripheral surface 32 of the intermediate layer 30 and the inner peripheral surface 52 of the outer layer 50, between the first braid 22 and the second braid 42. The anchoring effect between the proximal end portion 80a and the outer peripheral surface 32 of the intermediate layer 30 and the anchoring effect between the proximal end portion 80a and the inner peripheral surface 52 of the outer layer 50 increase the joining strength between the intermediate layer 30 and the tip 70a and the joining strength between the outer layer 50 and the tip 70a, respectively. In other words, the joining strength between the catheter shaft 60 and the tip 70a is increased. As a result, it is possible to further prevent the tip 70a from easily detaching from the catheter shaft 60.

Next, a catheter 1b of the disclosed embodiments will be described with reference to FIG. 8. Explaining only differences from the catheter 1 illustrated in FIG. 2, in the catheter 1b, the thickness of a proximal end portion 80b of a tip 70b increases in the distal direction (in other words, the thickness of the proximal end portion 80b decreases in the proximal direction). In this manner, the thickness of the proximal end portion 80b is largest at the boundary portion between the tip 70b and the catheter shaft 60, which can further reduce a risk that the tip 70b will break at the boundary portion even when stress is concentrated at the boundary portion.

Figure 8:
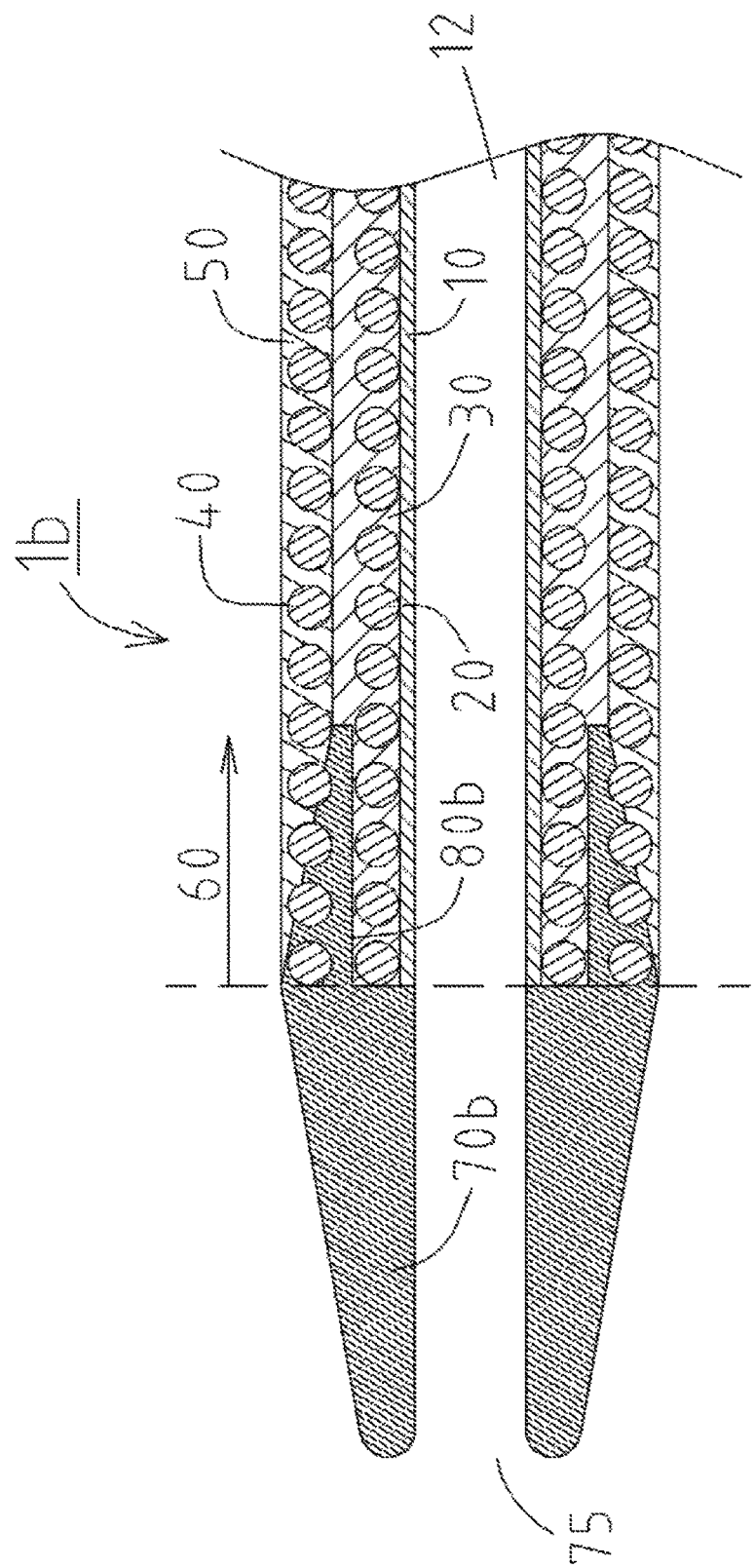
FIG. 8 is a cross-sectional view illustrating a part of a catheter according to the disclosed embodiments.

Moreover, the proximal end portion 80b of the tip 70b covers a distal end portion of the second coil body 40 (see FIG. 8). Thus, even when the technician operates the catheter 1b while the tip 70b is caught by a stenosis site or blockage, the anchoring effect between the proximal end portion 80b of the tip 70b and the second coil body 40 can further reduce a risk that the tip 70b will detach from the catheter shaft 60.

Next, a catheter 2b of the disclosed embodiments will be described with reference to FIG. 9. Explaining only differences from the catheter 2 illustrated in FIG. 3, in the catheter 2b, the thickness of the proximal end portion 80b of the tip 70b increases in the distal direction (in other words, the thickness of the proximal end portion 80b decreases in the proximal direction). In this manner, the thickness of the proximal end portion 80b is largest at the boundary portion between the tip 70b and the catheter shaft 60, which can further reduce a risk that the tip 70b will break at the boundary portion even when stress is concentrated at the boundary portion.

Figure 9:
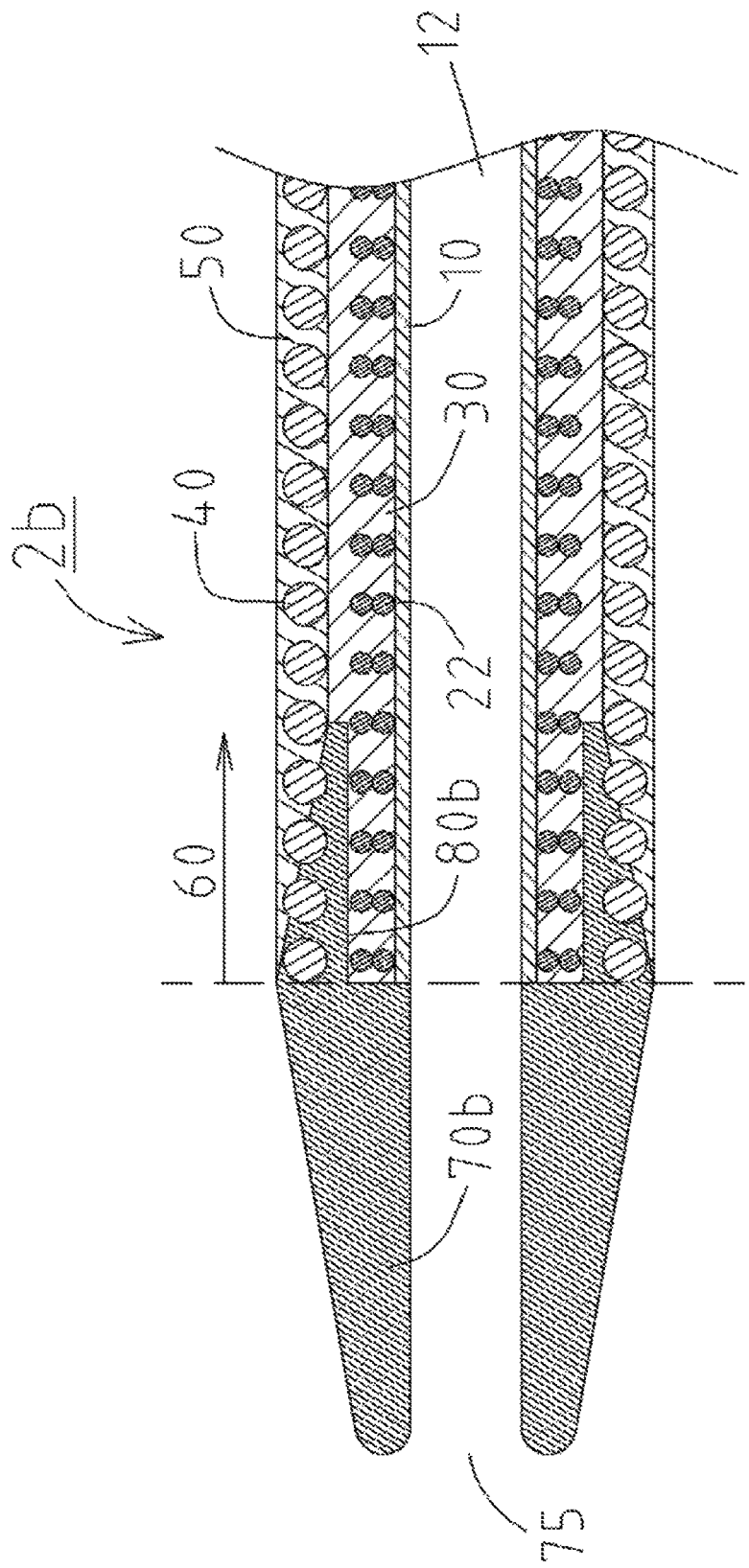
FIG. 9 is a cross-sectional view illustrating a part of a catheter according to the disclosed embodiments.

Moreover, the proximal end portion 80b of the tip 70b covers a distal end portion of the second coil body 40 (see FIG. 9). Thus, even when the technician operates the catheter 2b while the tip 70b is caught by a stenosis site or blockage, the anchoring effect between the proximal end portion 80b of the tip 70b and the second coil body 40 can further reduce a risk that the tip 70b will detach from the catheter shaft 60.

Next, a catheter 3b of the disclosed embodiments will be described with reference to FIG. 10. Explaining only differences from the catheter 3 illustrated in FIG. 4, in the catheter 3b, the thickness of the proximal end portion 80b of the tip 70b increases in the distal direction (in other words, the thickness of the proximal end portion 80b decreases in the proximal direction). In this manner, the thickness of the proximal end portion 80b is largest at the boundary portion between the tip 70b and the catheter shaft 60, which can further reduce a risk that the tip 70b will break at the boundary portion even when stress is concentrated at the boundary portion.

Figure 10:
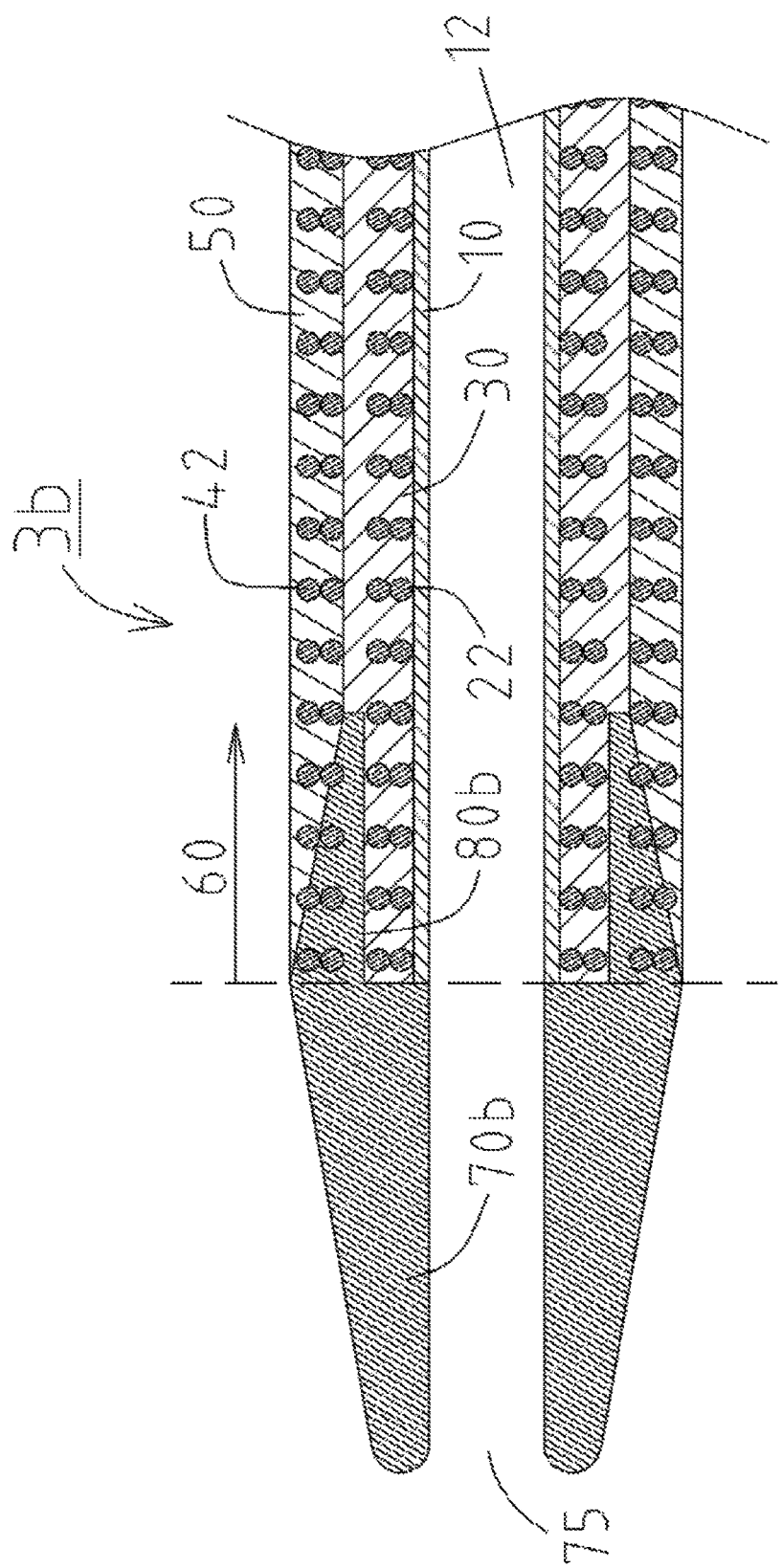
FIG. 10 is a cross-sectional view illustrating a part of a catheter according to the disclosed embodiments.

Moreover, the proximal end portion 80b of the tip 70b covers a distal end portion of the second braid 42 (see FIG. 10). Thus, even when the technician operates the catheter 3b while the tip 70b is caught by a stenosis site or blockage, the anchoring effect between the proximal end portion 80b of the tip 70b and the second braid 42 can further reduce a risk that the tip 70b will detach from the catheter shaft 60.

Next, a catheter 1c of the disclosed embodiments will be described with reference to FIG. 11. Explaining only differences from the catheter 1a illustrated in FIG. 5, in the catheter 1c, at least a distal portion of the outer layer 50 has a thickness that decreases toward the distal end, and includes an inclined uneven inner peripheral surface 52a (see FIG. 11). Then, a tip 70c includes a proximal end portion 80c joined to the outer peripheral surface 32 of the intermediate layer 30 and the inner peripheral surface 52a of the outer layer 50, between the first coil body 20 and the second coil body 40. The thickness of the proximal end portion 80c of the tip 70c increases in the distal direction (in other words, the thickness of the proximal end portion 80c decreases in the proximal direction).

In this manner, in the catheter 1c, the thickness of the proximal end portion 80c is largest at the boundary portion between the tip 70c and the catheter shaft 60, which can further reduce a risk that the tip 70c will break at the boundary portion even when stress is concentrated at the boundary portion. Moreover, the anchoring effect between the proximal end portion 80c and the outer peripheral surface 32 of the intermediate layer 30 and the anchoring effect between the proximal end portion 80c and the inner peripheral surface 52a of the outer layer 50 further increase the joining strength between the intermediate layer 30 and the tip 70c and the joining strength between the outer layer 50 and the tip 70c, respectively. In other words, the joining strength between the catheter shaft 60 and the tip 70c is increased. As a result, it is possible to further prevent the tip 70c from easily detaching from the catheter shaft 60.

Figure 11:
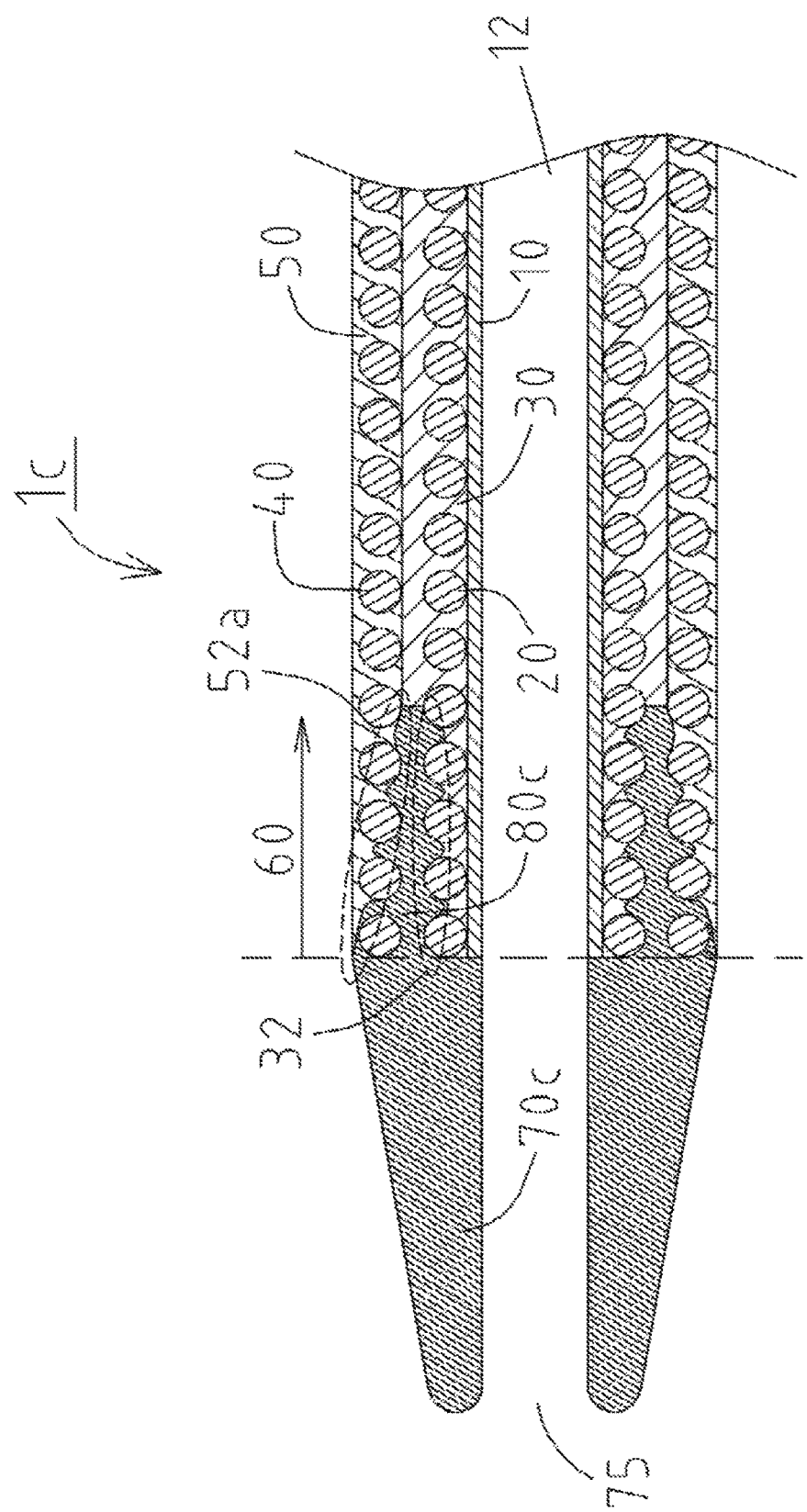
FIG. 11 is a cross-sectional view illustrating a part of a catheter according to the disclosed embodiments.

Moreover, the proximal end portion 80c of the tip 70c covers a distal end portion of the second coil body 40 (see FIG. 11). Thus, even when the technician operates the catheter 1c while the tip 70c is caught by a stenosis site or blockage, the anchoring effect between the proximal end portion 80c of the tip 70c and the second coil body 40 can further reduce a risk that the tip 70c will detach from the catheter shaft 60.

Next, a catheter 2c of the disclosed embodiments will be described with reference to FIG. 12. Explaining only differences from the catheter 2a illustrated in FIG. 6, in the catheter 2c, at least a distal portion of the outer layer 50 has a thickness that decreases toward the distal end, and includes the inclined uneven inner peripheral surface 52a (see FIG. 12). Then, the tip 70c includes the proximal end portion 80c joined to the outer peripheral surface 32 of the intermediate layer 30 and the inner peripheral surface 52a of the outer layer 50, between the first braid 22 and the second coil body 40. The thickness of the proximal end portion 80c of the tip 70c increases in the distal direction (in other words, the thickness of the proximal end portion 80c decreases in the proximal direction).

In this manner, in the catheter 2c, the thickness of the proximal end portion 80c is largest at the boundary portion between the tip 70c and the catheter shaft 60, which can further reduce a risk that the tip 70c will break at the boundary portion even when stress is concentrated at the boundary portion. Moreover, the anchoring effect between the proximal end portion 80c and the outer peripheral surface 32 of the intermediate layer 30 and the anchoring effect between the proximal end portion 80c and the inner peripheral surface 52a of the outer layer 50 further increase the joining strength between the intermediate layer 30 and the tip 70c and the joining strength between the outer layer 50 and the tip 70c, respectively. In other words, the joining strength between the catheter shaft 60 and the tip 70c is increased. As a result, it is possible to further prevent the tip 70c from easily detaching from the catheter shaft 60.

Figure 12:
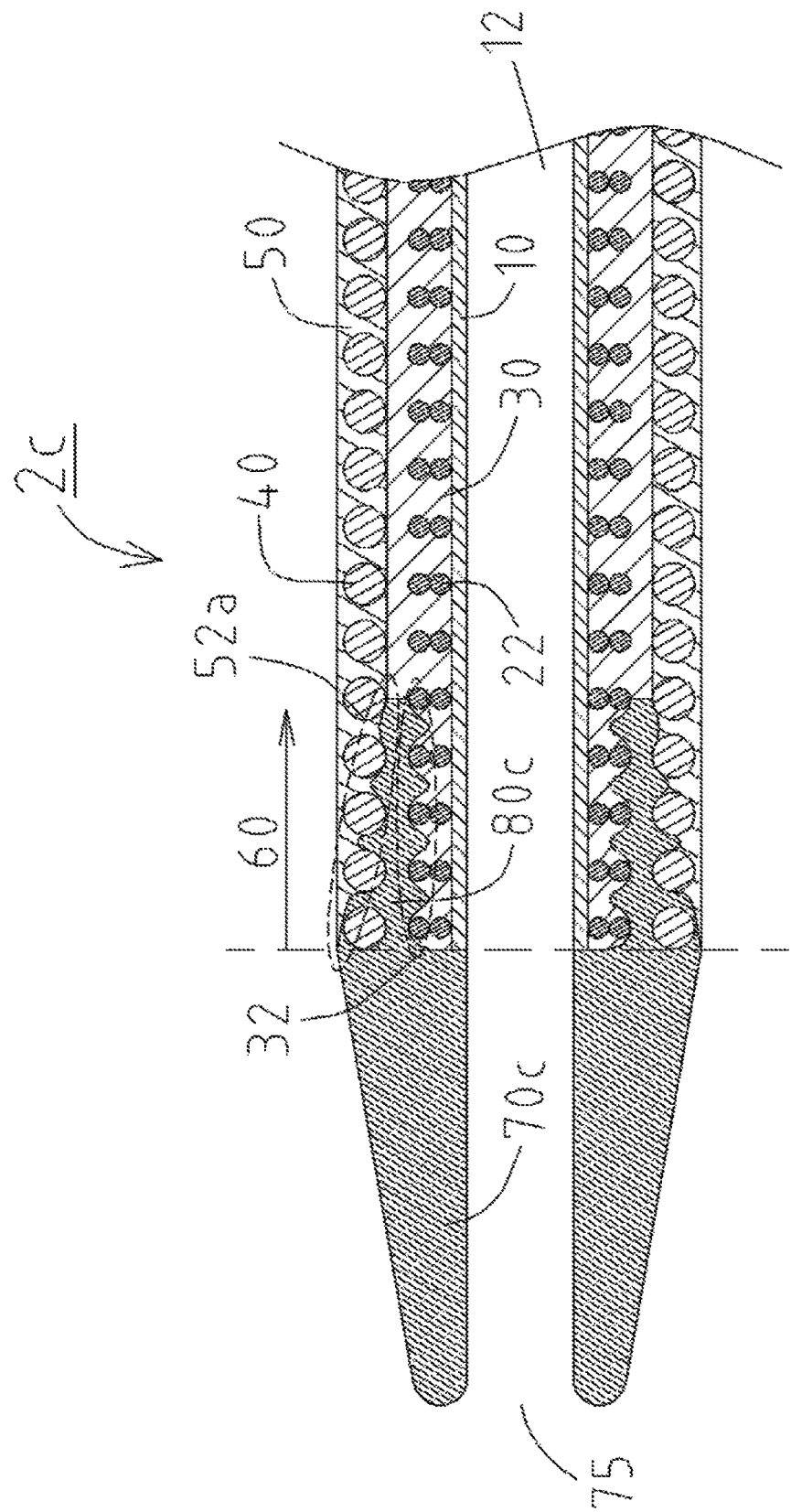
FIG. 12 is a cross-sectional view illustrating a part of a catheter according to the disclosed embodiments.

Moreover, the proximal end portion 80c of the tip 70c covers a distal end portion of the second coil body 40 (see FIG. 12). Thus, even when the technician operates the catheter 2c while the tip 70c is caught by a stenosis site or blockage, the anchoring effect between the proximal end portion 80c of the tip 70c and the second coil body 40 can further reduce a risk that the tip 70c will detach from the catheter shaft 60.

Next, a catheter 3c of the disclosed embodiments will be described with reference to FIG. 13. Explaining only differences from the catheter 3a illustrated in FIG. 7, in the catheter 3c, at least a distal portion of the outer layer 50 has a thickness that decreases toward the distal end, and includes the inclined uneven inner peripheral surface 52a (see FIG. 13). Then, the tip 70c includes the proximal end portion 80c joined to the outer peripheral surface 32 of the intermediate layer 30 and the inner peripheral surface 52a of the outer layer 50, between the first braid 22 and the second braid 42. The thickness of the proximal end portion 80c of the tip 70c increases in the distal direction (in other words, the thickness of the proximal end portion 80c decreases in the proximal direction).

In this manner, in the catheter 3c, the thickness of the proximal end portion 80c is largest at the boundary portion between the tip 70c and the catheter shaft 60, which can further reduce a risk that the tip 70c will break at the boundary portion even when stress is concentrated at the boundary portion. Moreover, the anchoring effect between the proximal end portion 80c and the outer peripheral surface 32 of the intermediate layer 30 and the anchoring effect between the proximal end portion 80c and the inner peripheral surface 52a of the outer layer 50 can further increase the joining strength between the intermediate layer 30 and the tip 70c and the joining strength between the outer layer 50 and the tip 70c, respectively. In other words, the joining strength between the catheter shaft 60 and the tip 70c is increased. As a result, it is possible to further prevent the tip 70c from easily detaching from the catheter shaft 60.

Figure 13:
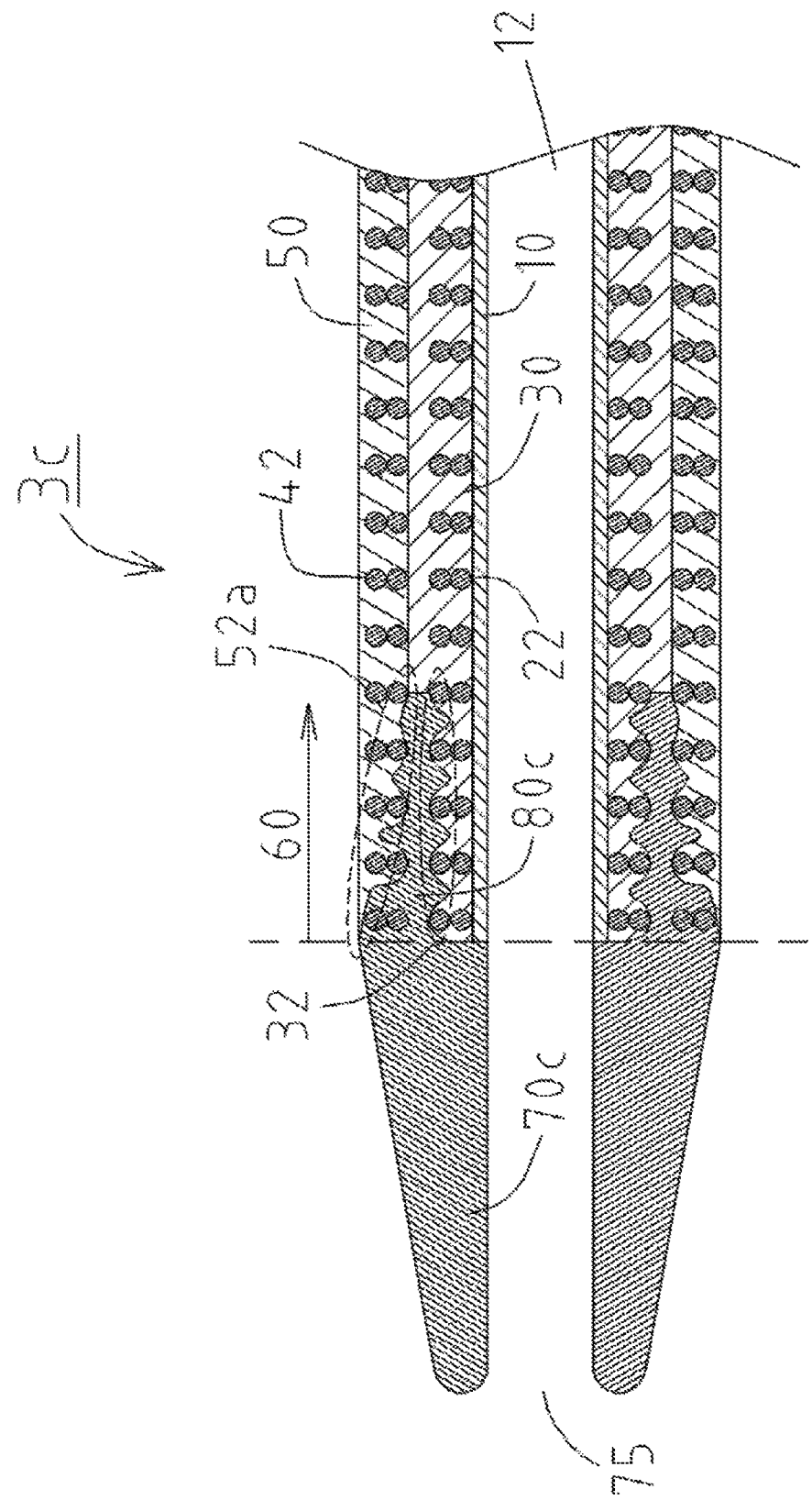
FIG. 13 is a cross-sectional view illustrating a part of a catheter according to the disclosed embodiments.

Moreover, the proximal end portion 80c of the tip 70c covers a distal end portion of the second braid 42 (see FIG. 13). Thus, even when the technician operates the catheter 3c while the tip 70c is caught by a stenosis site or blockage, the anchoring effect between the proximal end portion 80c of the tip 70c and the second braid 42 can further reduce a risk that the tip 70c will detach from the catheter shaft 60.

Figure 14:
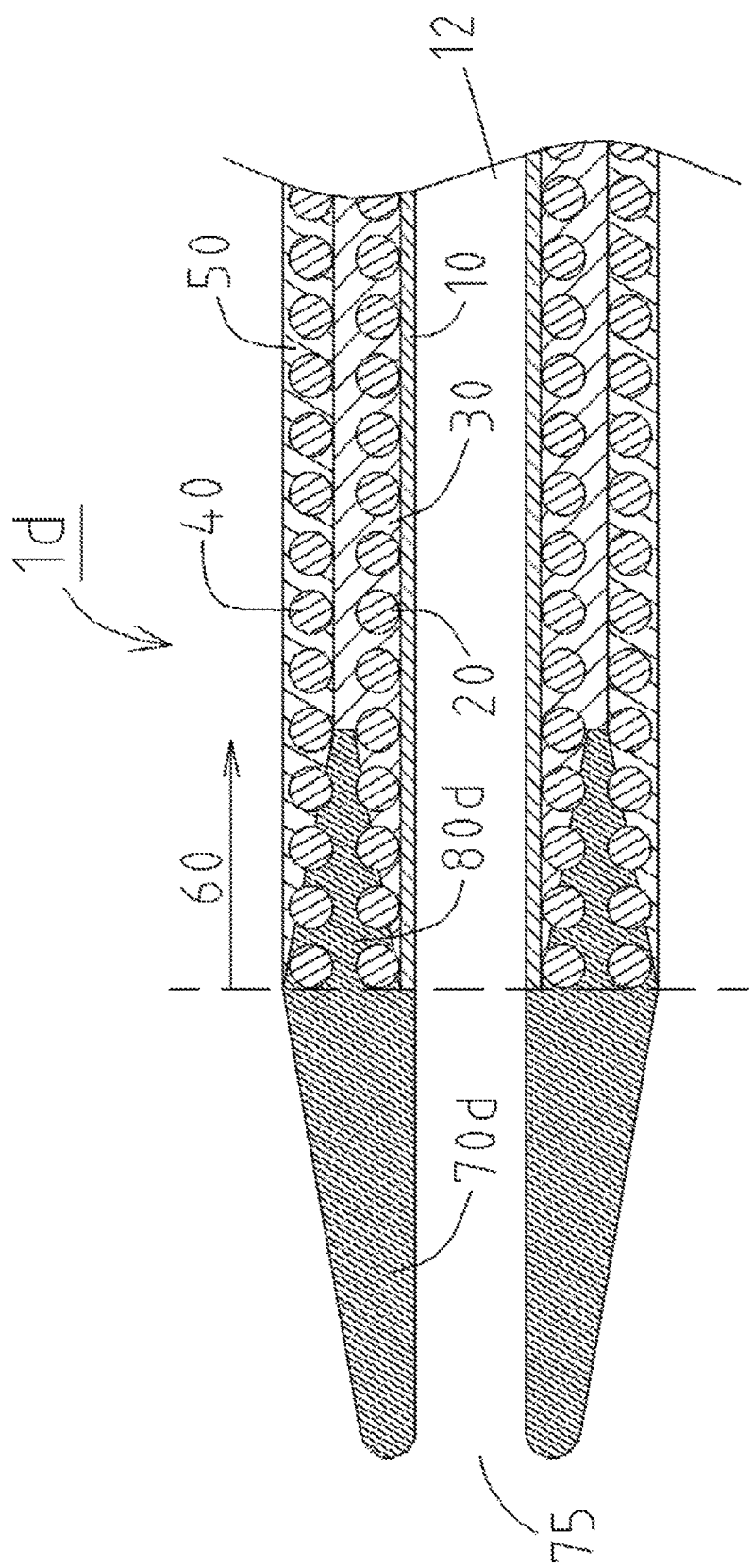
FIG. 14 is a cross-sectional view illustrating a part of a catheter according to the disclosed embodiments.

Note that in the catheter 1b illustrated in FIG. 8, the thickness of the proximal end portion 80b of the tip 70b increases in the distal direction only on the side of the second reinforcing layer (the second coil body 40). That is, the proximal end portion 80b has an inclined surface only on the side of the second reinforcing layer. However, the embodiment is not limited thereto. As illustrated in a catheter 1d of FIG. 14, the thickness of a proximal end portion 80d of a tip 70d may increase in the distal direction not only on the side of the second reinforcing layer (the second coil body 40) but also on the side of the first reinforcing layer (the first coil body 20). By contrast, the thickness of the proximal end portion 80d of the tip 70d may increase in the distal direction only on the side of the first reinforcing layer (the first coil body 20).

Similarly, in the catheters 2b, 3b illustrated in FIG. 9 and FIG. 10, the thickness of the proximal end portion 80b of the tip 70b may increase in the distal direction not only on the side of the second reinforcing layer (the second coil body 40 or the second braid 42) but also on the side of the first reinforcing layer (the first braid 22). By contrast, the thickness of the proximal end portion 80b of the tip 70b may increase in the distal direction only on the side of the first reinforcing layer (the first braid 22).

Figure 15:
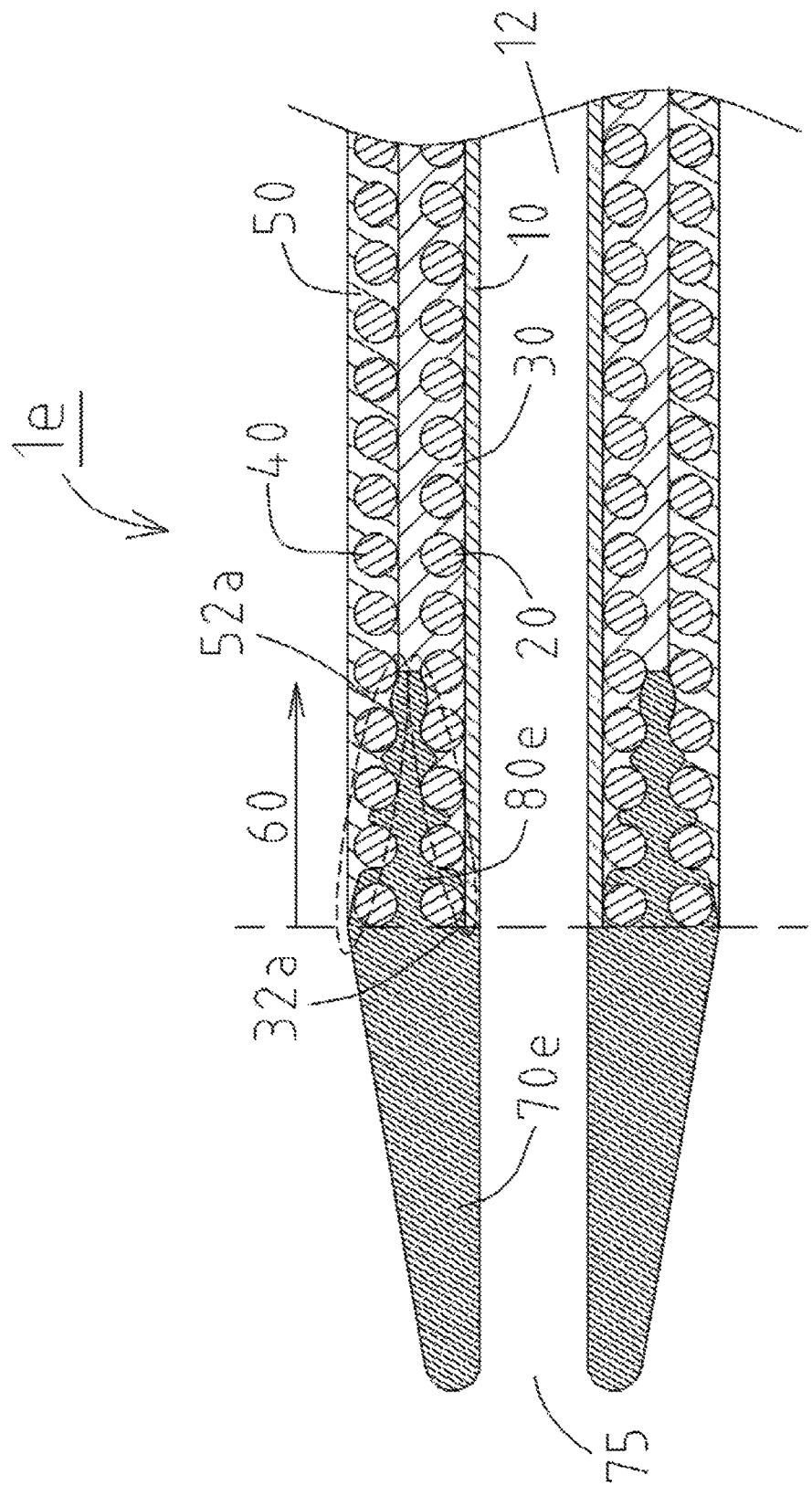
FIG. 15 is a cross-sectional view illustrating a part of a catheter according to the disclosed embodiments.

Note that in the catheter 1c illustrated in FIG. 11, the thickness of the proximal end portion 80c of the tip 70c increases in the distal direction only on the side of the second reinforcing layer (the second coil body 40). However, the embodiments are not limited thereto. As illustrated in a catheter 1e of FIG. 15, the thickness of a proximal end portion 80e of a tip 70e may increase in the distal end direction not only on the side of the second reinforcing layer (the second coil body 40) but also on the side of the first reinforcing layer (the first coil body 20). In the catheter 1e, the intermediate layer 30 includes an inclined uneven outer peripheral surface 32a, and the outer layer 50 includes the inclined uneven inner peripheral surface 52a (see FIG. 15). By contrast, the thickness of the proximal end portion 80d of the tip 70d may increase in the distal direction only on the side of the first reinforcing layer (the first coil body 20).

Similarly, in the catheters 2c, 3c illustrated in FIG. 12 and FIG. 13, the thickness of the proximal end portion 80c of the tip 70c may increase in the distal direction not only on the side of the second reinforcing layer (the second coil body 40 or the second braid 42) but also on the side of the first reinforcing layer (the first braid 22). By contrast, the thickness of the proximal end portion 80c of the tip 70c may increase in the distal direction only on the side of the first reinforcing layer (the first braid 22).

In the above description, there are exemplified the first coil body 20 or the first braid 22 as the first reinforcing layer, and the second coil body 40 or the second braid 42 as the second reinforcing layer. However, the embodiments are not limited thereto, and there may be used, as the first reinforcing layer or the second reinforcing layer, a metal hypo tube with a helical groove.

Moreover, in the above description, the proximal end portions 80, 80a, 80b, 80c, 80d, 80e of the tips 70, 70a, 70b, 70c, 70d, 70e are joined to the intermediate layer 30 and the outer layer 50. However, the embodiments are not limited thereto, and they may be joined to at least one of the intermediate layer 30 and the outer layer 50. Furthermore, the proximal end portions 80a, 80c, 80e of the tips 70a, 70c, 70e are joined to the uneven outer peripheral surfaces 32, 32a of the intermediate layer 30 and the uneven inner peripheral surfaces 52, 52a of the outer layer 50. However, the embodiments are not limited thereto, and they may be joined to at least one of the uneven outer peripheral surfaces 32, 32a of the intermediate layer 30 and the uneven inner peripheral surfaces 52, 52a of the outer layer 50.

In addition, in the cross-sectional views illustrated in FIG. 2 to FIG. 15, the proximal end portions 80, 80a, 80b, 80c, 80d, 80e of the tips 70, 70a, 70b, 70c, 70d, 70e are formed on both the upper and lower sides (in other words, on the entire periphery) between the first reinforcing layer (the first coil body 20 or the first braid 22) and the second reinforcing layer (the second coil body 40 or the second braid 42). However, the embodiments are not limited thereto, and they may be formed on only one side (in other words, at a certain part).

What is claimed is:

1. A catheter comprising:
  a catheter shaft including:
    an inner layer;
    a first reinforcing layer formed by wound one or more first wires and disposed around an outer periphery of the inner layer;
    an intermediate layer that covers the first reinforcing layer;
    a second reinforcing layer formed by wound one or more second wires and disposed around an outer periphery of the intermediate layer; and
    an outer layer that covers the second reinforcing layer; and
  a tip joined to a distal end of the catheter shaft, wherein the tip includes a proximal end portion that extends proximally in an axial direction of the catheter and that is joined to at least one of the intermediate layer and the outer layer, between the first reinforcing layer and the second reinforcing layer, and
  the proximal end portion penetrates into gaps between adjacent windings of the one or more first wires and/or the one or more second wires.

2. The catheter according to claim 1, wherein:
  the intermediate layer includes an uneven outer peripheral surface,
  the outer layer includes an uneven inner peripheral surface, and
  the proximal end portion of the tip is joined to at least one of the outer peripheral surface of the intermediate layer and the inner peripheral surface of the outer layer.

3. The catheter according to claim 2, wherein a thickness of the proximal end portion of the tip increases in a distal direction.

4. The catheter according to claim 2, wherein at least a distal portion of the outer layer has a thickness that decreases toward the distal end and includes an inclined inner peripheral surface.

5. The catheter according to claim 2, wherein the uneven outer peripheral surface of the intermediate layer and the uneven inner peripheral surface of the outer layer extend along an entire length of the proximal end portion of the tip.

6. The catheter according to claim 1, wherein a thickness of the proximal end portion of the tip increases in a distal direction.

7. The catheter according to claim 6, wherein an inner peripheral surface of the proximal end portion of the tip is inclined.

8. The catheter according to claim 7, wherein an outer peripheral surface of the proximal end portion of the tip is inclined.

9. The catheter according to claim 6, wherein an outer peripheral surface of the proximal end portion of the tip is inclined.

10. The catheter according to claim 6, wherein the proximal end portion of the tip covers a distal end portion of the second reinforcing layer.

11. The catheter according to claim 1, wherein at least a distal portion of the outer layer has a thickness that decreases toward the distal end and includes an inclined inner peripheral surface.

12. The catheter according to claim 1, wherein at least one of the first reinforcing layer and the second reinforcing layer is a coil body.

13. The catheter according to claim 1, wherein at least one of the first reinforcing layer and the second reinforcing layer is a braid.

* * * * *